US009885044B2

(12) United States Patent
Yu et al.

(10) Patent No.: US 9,885,044 B2
(45) Date of Patent: Feb. 6, 2018

(54) POLYNUCLEOTIDES AND METHODS FOR INHIBITING CANCER CELLS

(71) Applicant: Chang Gung Memorial Hospital, Linkou, Taoyuan (TW)

(72) Inventors: John Yu, Taoyuan (TW); Huan-Chieh Cho, Taoyuan (TW); Alice Yu, Taoyuan (TW)

(73) Assignee: Chang Gung Memorial Hospital, Linkou, Taoyuan (TW)

( * ) Notice: Subject to any disclaimer, the term of this patent is extended or adjusted under 35 U.S.C. 154(b) by 0 days.

(21) Appl. No.: 15/179,565

(22) Filed: Jun. 10, 2016

(65) Prior Publication Data

US 2016/0362690 A1 Dec. 15, 2016

Related U.S. Application Data

(60) Provisional application No. 62/174,572, filed on Jun. 12, 2015, provisional application No. 62/198,290, filed on Jul. 29, 2015.

(51) Int. Cl.
| | |
|---|---|
| *C12N 15/113* | (2010.01) |
| *A61K 31/7105* | (2006.01) |
| *A61K 31/05* | (2006.01) |
| *A61K 31/352* | (2006.01) |
| *A61K 31/135* | (2006.01) |

(52) U.S. Cl.
CPC ............ *C12N 15/113* (2013.01); *A61K 31/05* (2013.01); *A61K 31/135* (2013.01); *A61K 31/352* (2013.01); *A61K 31/7105* (2013.01); *C12N 2310/14* (2013.01); *C12N 2310/531* (2013.01); *C12N 2320/30* (2013.01); *C12N 2320/32* (2013.01)

(58) Field of Classification Search
None
See application file for complete search history.

(56) References Cited

U.S. PATENT DOCUMENTS

2013/0202678 A1* 8/2013 Yu ..................... A61K 48/005
424/450

FOREIGN PATENT DOCUMENTS

| CN | 102836149 A | 12/2012 |
| CN | 103784962 A | 5/2014 |
| WO | WO 2011129427 A1 | 10/2011 |

OTHER PUBLICATIONS

Stina Garvin, et al.; "{Resveratrol Induces Apoptosis and Inhibits Angiogenesis in Human Breast Cancer Xenografts In Vivo"; Cancer Letters 231; (2006); 113-122; 10 pgs.
Alexander Schlachterman, et al.; "Combined Resveratrol Quercetin, and Catechin Treatment Reduces Breast Tumor Growth in a Nude Mouse Model"; Translational Oncology, Neoplasia Press, US, vol. 1, No. 1, Mar. 1, 2008; pp. 19-27, XP002604473.

* cited by examiner

*Primary Examiner* — Tracy Vivlemore
(74) *Attorney, Agent, or Firm* — Muncy, Geissler, Olds & Lowe, P.C.

(57) ABSTRACT

The present invention provides methods of inhibiting or reducing the growth of cancer cells in a subject, by administering a therapeutic effective amount of Puf-A inhibitor, whereby the symptoms and signs of cancer in the subject are reduced. Also provided are polynucleotides and vectors encoding the shRNAs which target Puf-A expression, which are useful for the treatment of cancer.

14 Claims, 17 Drawing Sheets
(5 of 17 Drawing Sheet(s) Filed in Color)

Fig. 6A

ATGGAAGTTAAAGGGAAAAAGCAATTCACAGGAAAGAGTACAAAGACAG
CACAAGAAAAAAACAGATTTCATAAAAATAGTGATTCTGGTTCTTCAAAGA
CATTTCCAACAAGGAAAGTTGCTAAAGAAGGTGGACCTAAAGTCACATCTA
GGAACTTTGAGAAAGTATCACAAAACTTGGGAAAAAGGGTGTAAAGCAG
TTCAAGAATAAGCAGCAAGGGGACAAATCACCAAAGAACAAATTCCAGCC
GGCAAATAAATTCAACAAGAAGAGAAAATTCCAGCCAGATGGTAGAAGCG
ATGAATCAGCAGCCAAGAAGCCCAATGGGATGACTTCAAAAAGAAGAAG
AAAGAACTGAAGCAAAGCAGACAACTCAGTGATAAAACCAACTATGACAT
TGTTGTTCGGGCAAAGCAGATGTGGGAGATTTTAAGAAGAAAAGACTGTG
ACAAAGAAAAAAGAGTAAAGTTAATGAGTGATTTGCAGAAGTTGATTCAA
GGGAAAATTAAAACTATTGCATTTGCACACGATTCAACTCGTGTGATCCAG
TGTTACATTCAGTATGGTAATGAAGAACAGAGAAAACAGGCTTTTGAAGAA
TTGCGAGATGATTTGGTTGAGTTAAGTAAAGCCAAATATTCGAGAAATATTG
TTAAGAAATTTCTCATGTATGGAAGTAAACCACAGATTGCAGAGATAATCA
GAAGTTTTAAAGGCCACGTGAGGAAGATGCTGCGGCATGCGGAAGCATCA
GCCATCGTGGAGTACGCATACAATGACAAAGCCATTTTGGAGCAGAGGAA
CATGCTGACGGAAGAGCTCTATGGGAACACATTTCAGCTTTACAAGTCAGC
AGATCACCGAACTCTGGACAAAGTGTTAGAGGTACAGCCAGAAAAATTAG
AACTTATTATGGATGAAATGAAACAGATTCTAACTCCAATGGCCCAAAAGG
AAGCTGTGATTAAGCACTCATTGGTGCATAAAGTATTCTTGGACTTTTTAC
CTATGCACCCCCCAAACTCAGATCAGAAATGATTGAAGCCATCCGCGAAGC
GGTGGTCTACCTGGCACACACACACGATGGCGCCAGAGTGGCCATGCACT
GCCTGTGGCATGGCACGCCCAAGGACAGGAAAGTGATTGTGAAAACAATG
AAGACTTATGTTGAAAAGGTGGCTAATGGCCAATACTCCCATTTGGTTTTAC
TGGCGGCATTTGATTGTATTGATGATACTAAGCTTGTGAAGCAGATAATCATA
TCAGAAATTATCAGTTCATTGCCTAGCATAGTAAATGACAAATATGGAAGGA
AGGTCCTATTGTACTTACTAAGCCCCAGAGATCCTGCACATACAGTACGAG
AAATCATTGAAGTTCTGCAAAAAGGAGATGGAAATGCACACAGTAAGAAA
GATACAGAGGTCCGCAGACGGGAGCTCCTAGAATCCATTTCTCCAGCTTTG
TTAAGCTACCTGCAAGAACACGCCCAAGAAGTGGTGCTAGATAAGTCTGC
GTGTGTGTTGGTGTCTGACATTCTGGGATCTGCCACTGGAGACGTTCAGCC
TACCATGAATGCCATCGCCAGCTTGGCAGCAACAGGACTGCATCCTGGTGG
CAAGGACGGAGAGCTTCACATTGCAGAACATCCTGCAGGACATCTAGTTCT
GAAGTGGTTAATAGAGCAAGATAAAAGATGAAAGAAATGGGAGAGAAG
GTTGTTTTGCAAAAACACTTGTAGAGCATGTTGGTATGAAGAACCTGAAGT
CCTGGGCTAGTGTAAATCGAGGTGCCATTATTCTTTCTAGCCTCCTCCAGAG

Fig. 6A (Cont.)
TTGTGACCTGGAAGTTGCAAACAAAGTCAAAGCTGCACTGAAAAGCTTGATTCCT
ACATTGGAAAAAACCAAAAGCACCAGCAAAGGAATAGAAATTCTACTTGAAAAA
CTGAGCACATAG
Fig. 6B
shPuf-A-1, SEQ ID NO:2
CCGGGCCTAGCATAGTAAATGACAACTCGAGTTGTCATTTACTATGCTAGGCTTTTT
TG
shPuf-A-2, SEQ ID NO:3
CCGGCGTGTGATCCAGTGTTACATTCTCGAGAATGTAACACTGGATCACACGTTTT
TG
Fig. 6C
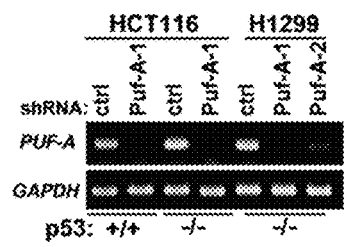
Fig. 6D
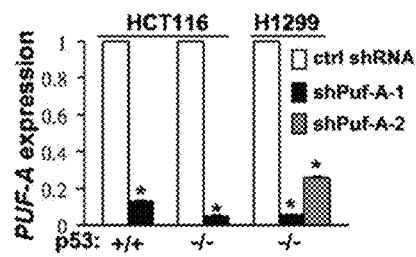

SEQUENCE LISTING

<160> NUMBER OF SEQ ID NOS: 4

<210> SEQ ID NO 1
<211> LENGTH: 1947
<212> TYPE: DNA
<213> ORGANISM: Homo sapiens

<400> SEQUENCE: 1

| | | | | | | |
|---|---|---|---|---|---|---|
| atggaagtta | aagggaaaaa | gcaattcaca | ggaaagagta | caaagacagc | acaagaaaaa | 60 |
| aacagatttc | ataaaaatag | tgattctggt | tcttcaaaga | catttccaac | aaggaaagtt | 120 |
| gctaaagaag | gtggacctaa | agtcacatct | aggaactttg | agaaagtat | cacaaaactt | 180 |
| gggaaaaagg | gtgtaaagca | gttcaagaat | aagcagcaag | gggacaaatc | accaaagaac | 240 |
| aaattccagc | cggcaaataa | attcaacaag | aagagaaaat | tccagccaga | tggtagaagc | 300 |
| gatgaatcag | cagccaagaa | gcccaaatgg | gatgacttca | aaaagaagaa | gaaagaactg | 360 |
| aagcaaagca | gacaactcag | tgataaaacc | aactatgaca | ttgttgttcg | ggcaaagcag | 420 |
| atgtgggaga | ttttaagaag | aaaagactgt | gacaaagaaa | aaagagtaaa | gttaatgagt | 480 |
| gatttgcaga | agttgattca | agggaaaatt | aaaactattg | catttgcaca | cgattcaact | 540 |
| cgtgtgatcc | agtgttacat | tcagtatggt | aatgaagaac | agagaaaaca | ggcttttgaa | 600 |
| gaattgcgag | atgatttggt | tgagttaagt | aaagccaaat | attcgagaaa | tattgttaag | 660 |
| aaatttctca | tgtatggaag | taaaccacag | attgcagaga | taatcagaag | ttttaaggc | 720 |
| cacgtgagga | agatgctgcg | gcatgcggaa | gcatcagcca | tcgtggagta | cgcatacaat | 780 |
| gacaaagcca | ttttggagca | gaggaacatg | ctgacggaag | agctctatgg | gaacacattt | 840 |
| cagctttaca | agtcagcaga | tcaccgaact | ctggacaaag | tgttagaggt | acagccagaa | 900 |
| aaattagaac | ttattatgga | tgaaatgaaa | cagattctaa | ctccaatggc | ccaaaaggaa | 960 |
| gctgtgatta | agcactcatt | ggtgcataaa | gtattcttgg | actttttttac | ctatgcaccc | 1020 |
| cccaaactca | gatcagaaat | gattgaagcc | atccgcgaag | cggtggtcta | cctggcacac | 1080 |
| acacacgatg | cgccagagt | ggccatgcac | tgcctgtggc | atggcacgcc | caaggacagg | 1140 |
| aaagtgattg | tgaaaacaat | gaagacttat | gttgaaaagg | tggctaatgg | ccaatactcc | 1200 |
| catttggttt | tactggcggc | atttgattgt | attgatgata | ctaagcttgt | gaagcagata | 1260 |
| atcatatcag | aaattatcag | ttcattgcct | agcatagtaa | atgacaaata | tggaaggaag | 1320 |
| gtcctattgt | acttactaag | ccccagagat | cctgcacata | cagtacgaga | aatcattgaa | 1380 |
| gttctgcaaa | aaggagatgg | aaatgcacac | agtaagaaag | atacagaggt | ccgcagacgg | 1440 |
| gagctcctag | aatccatttc | tccagctttg | ttaagctacc | tgcaagaaca | cgcccaagaa | 1500 |
| gtggtgctag | ataagtctgc | gtgtgtgttg | gtgtctgaca | ttctgggatc | tgccactgga | 1560 |
| gacgttcagc | ctaccatgaa | tgccatcgcc | agcttggcag | caacaggact | gcatcctggt | 1620 |
| ggcaaggacg | gagagcttca | cattgcagaa | catcctgcag | gacatctagt | tctgaagtgg | 1680 |
| ttaatagagc | aagataaaaa | gatgaaagaa | aatgggagag | aaggttgttt | tgcaaaaaca | 1740 |
| cttgtagagc | atgttggtat | gaagaacctg | aagtcctggg | ctagtgtaaa | tcgaggtgcc | 1800 |
| attattcttt | ctagcctcct | ccagagttgt | gacctggaag | ttgcaaacaa | agtcaaagct | 1860 |
| gcactgaaaa | gcttgattcc | tacattggaa | aaaccaaaa | gcaccagcaa | aggaatagaa | 1920 |
| attctacttg | aaaaactgag | cacatag | | | | 1947 |

<210> SEQ ID NO 2
<211> LENGTH: 59

```
<212> TYPE: DNA
<213> ORGANISM: Artificial Sequence
<220> FEATURE:
<223> OTHER INFORMATION: shRNA for the Puf A gene

<400> SEQUENCE: 2
ccgggcctag catagtaaat gacaactcga gttgtcattt actatgctag cttttttg      59

<210> SEQ ID NO 3
<211> LENGTH: 58
<212> TYPE: DNA
<213> ORGANISM: Artificial Sequence
<220> FEATURE:
<223> OTHER INFORMATION: shRNA for the Puf A gene

<400> SEQUENCE: 3
ccggcgtgtg atccagtgtt acattctcga gaatgtaaca ctggatcaca cgttttttg     58

<210> SEQ ID NO 4
<211> LENGTH: 648
<212> TYPE: PRT
<213> ORGANISM: Homo sapiens

<400> SEQUENCE: 4

Met Glu Val Lys Gly Lys Lys Gln Phe Thr Gly Lys Ser Thr Lys Thr
1               5                   10                  15

Ala Gln Glu Lys Asn Arg Phe His Lys Asn Ser Asp Ser Gly Ser Ser
            20                  25                  30

Lys Thr Phe Pro Thr Arg Lys Val Ala Lys Glu Gly Gly Pro Lys Val
        35                  40                  45

Thr Ser Arg Asn Phe Glu Lys Ser Ile Thr Lys Leu Gly Lys Lys Gly
    50                  55                  60

Val Lys Gln Phe Lys Asn Lys Gln Gly Asp Lys Ser Pro Lys Asn
65                  70                  75                  80

Lys Phe Gln Pro Ala Asn Lys Phe Asn Lys Lys Arg Lys Phe Gln Pro
                85                  90                  95

Asp Gly Arg Ser Asp Glu Ser Ala Ala Lys Lys Pro Lys Trp Asp Asp
            100                 105                 110

Phe Lys Lys Lys Lys Lys Glu Leu Lys Gln Ser Arg Gln Leu Ser Asp
        115                 120                 125

Lys Thr Asn Tyr Asp Ile Val Val Arg Ala Lys Gln Met Trp Glu Ile
    130                 135                 140

Leu Arg Arg Lys Asp Cys Asp Lys Glu Lys Arg Val Lys Leu Met Ser
145                 150                 155                 160

Asp Leu Gln Lys Leu Ile Gln Gly Lys Ile Lys Thr Ile Ala Phe Ala
                165                 170                 175

His Asp Ser Thr Arg Val Ile Gln Cys Tyr Ile Gln Tyr Gly Asn Glu
            180                 185                 190

Glu Gln Arg Lys Gln Ala Phe Glu Glu Leu Arg Asp Asp Leu Val Glu
        195                 200                 205

Leu Ser Lys Ala Lys Tyr Ser Arg Asn Ile Val Lys Lys Phe Leu Met
    210                 215                 220

Tyr Gly Ser Lys Pro Gln Ile Ala Glu Ile Ile Arg Ser Phe Lys Gly
225                 230                 235                 240

His Val Arg Lys Met Leu Arg His Ala Glu Ala Ser Ala Ile Val Glu
                245                 250                 255

Tyr Ala Tyr Asn Asp Lys Ala Ile Leu Glu Gln Arg Asn Met Leu Thr
            260                 265                 270
```

```
Glu Glu Leu Tyr Gly Asn Thr Phe Gln Leu Tyr Lys Ser Ala Asp His
            275                 280                 285

Arg Thr Leu Asp Lys Val Leu Glu Val Gln Pro Glu Lys Leu Glu Leu
        290                 295                 300

Ile Met Asp Glu Met Lys Gln Ile Leu Thr Pro Met Ala Gln Lys Glu
305                 310                 315                 320

Ala Val Ile Lys His Ser Leu Val His Lys Val Phe Leu Asp Phe Phe
                325                 330                 335

Thr Tyr Ala Pro Pro Lys Leu Arg Ser Glu Met Ile Glu Ala Ile Arg
            340                 345                 350

Glu Ala Val Val Tyr Leu Ala His Thr His Asp Gly Ala Arg Val Ala
        355                 360                 365

Met His Cys Leu Trp His Gly Thr Pro Lys Asp Arg Lys Val Ile Val
370                 375                 380

Lys Thr Met Lys Thr Tyr Val Glu Lys Val Ala Asn Gly Gln Tyr Ser
385                 390                 395                 400

His Leu Val Leu Leu Ala Ala Phe Asp Cys Ile Asp Asp Thr Lys Leu
                405                 410                 415

Val Lys Gln Ile Ile Ile Ser Glu Ile Ile Ser Ser Leu Pro Ser Ile
            420                 425                 430

Val Asn Asp Lys Tyr Gly Arg Lys Val Leu Leu Tyr Leu Leu Ser Pro
        435                 440                 445

Arg Asp Pro Ala His Thr Val Arg Glu Ile Ile Glu Val Leu Gln Lys
    450                 455                 460

Gly Asp Gly Asn Ala His Ser Lys Lys Asp Thr Glu Val Arg Arg Arg
465                 470                 475                 480

Glu Leu Leu Glu Ser Ile Ser Pro Ala Leu Leu Ser Tyr Leu Gln Glu
                485                 490                 495

His Ala Gln Glu Val Val Leu Asp Lys Ser Ala Cys Val Leu Val Ser
            500                 505                 510

Asp Ile Leu Gly Ser Ala Thr Gly Asp Val Gln Pro Thr Met Asn Ala
        515                 520                 525

Ile Ala Ser Leu Ala Ala Thr Gly Leu His Pro Gly Gly Lys Asp Gly
    530                 535                 540

Glu Leu His Ile Ala Glu His Pro Ala Gly His Leu Val Leu Lys Trp
545                 550                 555                 560

Leu Ile Glu Gln Asp Lys Lys Met Lys Glu Asn Gly Arg Glu Gly Cys
                565                 570                 575

Phe Ala Lys Thr Leu Val Glu His Val Gly Met Lys Asn Leu Lys Ser
            580                 585                 590

Trp Ala Ser Val Asn Arg Gly Ala Ile Ile Leu Ser Ser Leu Leu Gln
        595                 600                 605

Ser Cys Asp Leu Glu Val Ala Asn Lys Val Lys Ala Ala Leu Lys Ser
    610                 615                 620

Leu Ile Pro Thr Leu Glu Lys Thr Lys Ser Thr Ser Lys Gly Ile Glu
625                 630                 635                 640

Ile Leu Leu Glu Lys Leu Ser Thr
                645
```

POLYNUCLEOTIDES AND METHODS FOR INHIBITING CANCER CELLS

CROSS-REFERENCE TO RELATED APPLICATIONS

This application claims the benefit of priority from U.S. Provisional Application No. 62/174,572, filed Jun. 12, 2015 and U.S. Provisional Application No. 62/198,290 filed Jul. 29, 2015, the entire contents of each of which are incorporated herein by reference.

BACKGROUND OF THE INVENTION

Puf family is an evolutionarily conserved protein family named after Pumilio (*Drosophila*) and FBF (Fem-3 mRNA-binding Factor, *Caenorhabditis elegans*). Puf family members are usually identified by the presence of eight tandem Puf repeats of ~35-39 amino acids and the repeat binds to specific sequences in the 39 untranslated region (UTR) of a target mRNA. The Puf-A gene was first reported by J. Yu et al. and was found to play an important role not only in eye development, but also in primordial germ-cell migration and the specification of germ cell lineage (J Yu et al., A Novel puf-A Gene Predicted from Evolutionary Analysis Is Involved in the Development of Eyes and Primordial Germ-Cells, PLoS ONE 4(3): e4980. doi:10.1371/journal.pone.0004980).

Cancer remains a major public health problem worldwide. Tumor Protein P53, a tumor suppressor gene, is the most frequently mutated gene in human cancer, with more than half of all human cancers carrying mutations in this particular gene. Notably, patients with mutated or deleted P53 have poorer prognosis and or higher drug resistance. Despite the advance in cancer therapy over the last few decades, the medical community still faces with the challenge of treating many types of cancer, especially mutated or deleted P53 cancer. Accordingly, there is still a need for a more effective and safe cancer treatment, especially for p53 deficient cancer. The present invention addresses this need and other needs.

BRIEF SUMMARY OF THE INVENTION

Accordingly, the present invention provide methods of inhibiting or killing cancer cells in a subject in need thereof, by contacting a therapeutically effective amount of Puf-A inhibitor with the cancer cell.

The present invention also provides methods to inhibit or kill cancer cells in a subject in need thereof, by administering an effective amount of a therapeutic agent to reduces or knock down the expression of Puf-A, and/or reduces Puf A's activity.

The present invention further provides methods of inhibiting cancer cells, by inhibiting Puf-A expression in the cancer cells.

In some embodiments, polynucleotides encoding a small hairpin RNA (shRNA) molecule to reduce Puf-A expression are provided. In some embodiments, the polynucleotide comprises a sequence of the Puf-A gene described herein.

In other embodiments, vectors comprising a promoter and a polynucleotide encoding an shRNA, wherein the nucleotide sequence of the polynucleotide is at least 90% homologous to SEQ ID NO:2 or SEQ ID NO:3, are also provided.

The present invention also discloses pharmaceutical compositions comprising the vector described herein and a pharmaceutically acceptable excipient or carrier.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

The invention will become more apparent when read with the accompanying figures and detailed description which follow.

BRIEF DESCRIPTION OF THE DRAWINGS

The patent or patent application contains at least one drawing executed in color. Copies of this patent or patent application with color drawings will be provided by the Office upon request and payment of the necessary fee.

Illustrative embodiments of the present invention are described in detail below with reference to the following Figures:

FIG. 3A shows the effect of Kras activation on Puf-A level in the control group and $Kras^{G12D}$ transduced group, using Western blot, RT-PCR and Q-PCR analyses. FIG. 3B shows the effect of c-Myc activation in the control group and c-Myc transduced group, using Western blot, RT-PCR and Q-PCR analyses. FIG. 3C is a series of bar graphs showing Puf-A promoter activity in $Kras^{G12D}$ or c-Myc transfected cells, determined by dual-luciferase reporter assay. FIG. 3D illustrates the binding of c-Myc protein to exon 1 of Puf-A locus in H1299 and HCT116 cells. FIG. 3E shows the effect of Kras depletion on Puf-A level in two Kras mutation cell lines, H460 ($Kras^{Q61H}$) and HCT116 ($Kras^{G13D}$), determined by Western blot, RT-PCR and Q-PCR analyses. FIG. 3F is an assembly of the Western blot images illustrating the effect of Raf inhibitor (Raf (i)), MEK1 inhibitor (PD98059) and MEK1/2 inhibitor (U0126) on the expression of Puf-A, phosphorylated ERK1/2, total ERK1/2 and β-actin in H460 ($Kras^{Q61H}$) and HCT116 ($Kras^{G13D}$) cancer cells.

FIG. 6A show the nucleotide sequence of human Puf-A gene (SEQ ID NO:1). FIG. 6B shows the nucleotide sequences of the polypeptides encoding shPuf-A-1 (SEQ ID NO:2) and shPuf-A-2 (SEQ ID NO:3). FIG. 6C and FIG. 6D illustrate the Puf-A knockdown efficiency of control shRNA, shPuf-A-1 and shPuf-A-2 in colorectal cancer cells (HCT116) and lung cancer cells (H1299), determined by RT-PCR and Q-PCR analyses.

DETAILED DESCRIPTION OF THE INVENTION

Definition

Figure 1A:
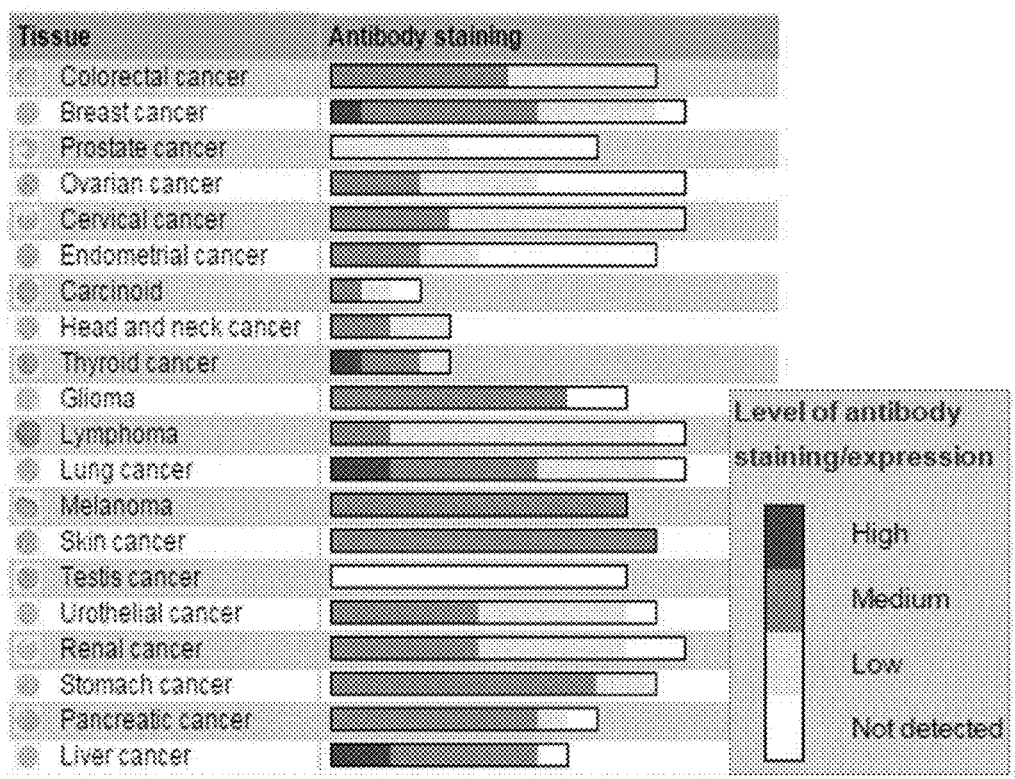
FIG. 1A illustrates the expression of Puf-A in various types of cancer.

As employed above and throughout the disclosure, the following terms, unless otherwise indicated, shall be understood to have the following meanings.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not in this specification. The specification is not intended to identify essential features of the claimed subject matter, nor is any portion of the specification to be used in isolation to determine the scope of the claimed subject matter. Claimed subject matter is to be understood by reference to appropriate portions of the entire specification, including all text and drawings and each claim.

As used herein, the singular forms "a," "an," and "the" include the plural reference unless the context clearly indicates otherwise.

An "effective amount," as used herein, includes a dose of an Puf-A inhibitor that is sufficient to reduce the symptoms and/or signs of cancer, which include, but are not limited to, weight loss, pain and tumor mass, which is detectable, either clinically as a palpable mass or radiologically through various imaging means.

The term "treating," "treated," or "treatment" as used herein includes preventative (e.g. prophylactic), palliative, and curative uses or results.

The term "inhibiting" and "reducing" includes slowing, preventing or stopping the growth of.

The term "subject" can refer to a vertebrate having cancer or to a vertebrate deemed to be in need of cancer treatment. Subjects include warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

Identity or homology with respect to a specified nucleic acid sequence of this invention is defined herein as the percentage of nucleic acid residues in a candidate sequence that are identical or homologous with the specified residues, after aligning the sequences and introducing gaps, if necessary, to achieve the maximum percent homology. Methods of alignment of nucleotide sequences for comparison are well known in the art. The NCBI Basic Local Alignment Search Tool (BLAST (Altschul et al, J. Mol. Biol. 215:403, 1990) is available from several sources, including the National Center for Biotechnology Information (NCBI, Bethesda, Md.) and on the internet, for use in connection with the sequence analysis programs, such as blastn. A description of how to determine sequence identity using this program is available on the NCBI website.

The term "polynucleotide" is intended to encompass a singular nucleic acid as well as plural nucleic acids, and refers to an isolated nucleic acid molecule or construct, e.g., messenger RNA (mRNA), virally-derived RNA, or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a therapeutic polypeptide contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

Recitation of ranges of values herein are merely intended to serve as a shorthand method of referring individually to each separate value falling within the range, unless otherwise indicated herein, and each separate value is incorporated into the specification as if it were individually recited herein. All numbers herein may be understood as modified by "about." In one embodiment, the term "about," when referring to a measurable value such as an amount, a temporal duration, and the like, is meant to encompass variations of ±10%, preferably ±5%, more preferably ±1%, and even more preferably ±0.1% from the specified value, as such variations are appropriate to the % of homology, unless other specified.

Methods of Inhibiting or Suppressing Cancer Cells Growth

Some embodiments of the invention are directed to methods of inhibiting cancer cell growth or killing cancer cells in a subject, which comprises the administration a therapeutic effective amount of Puf-A inhibitor to a subject in need thereof, whereby the symptoms and/or signs of the cancer in the subject are reduced.

Puf-A is a member of the highly conserved Puf family. SEQ ID NO:1 is the DNA sequence of human Puf-A gene and SEQ ID NO:4 is the amino acid sequence of human Puf-A gene. A higher Puf-A expression is correlated with a more advanced stage of cancer and a shorter survival rate, see Examples 1 and 2.

Figure 3A:
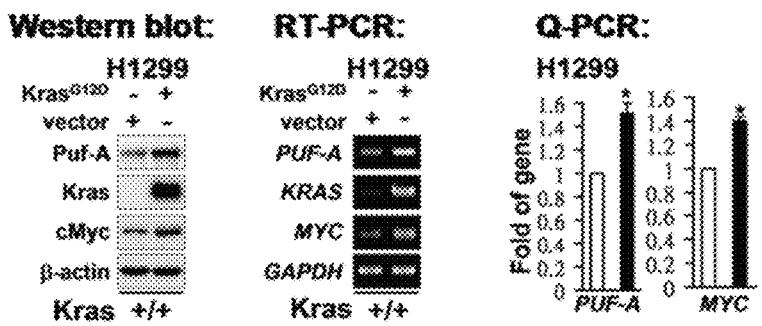
FIGS. 3A-3F are an assembly of images illustrating the effect of Kras on the expression of Puf-A.
Figure 3B:
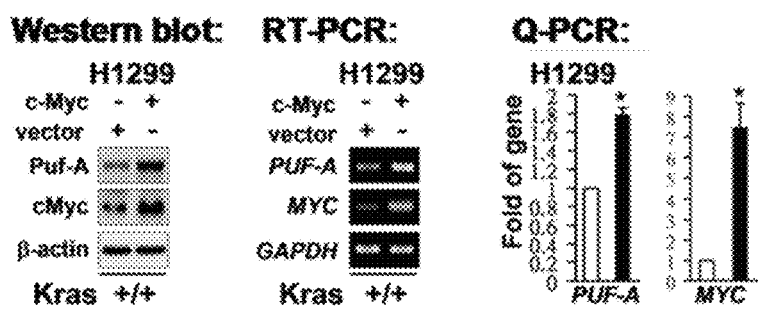
Figure 3C:
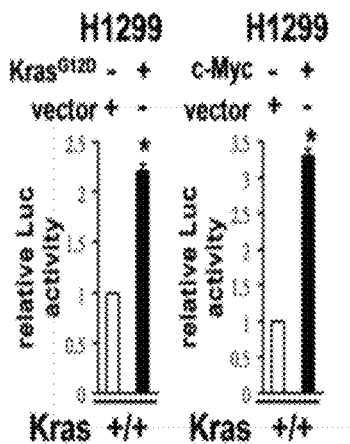
Figure 3D:
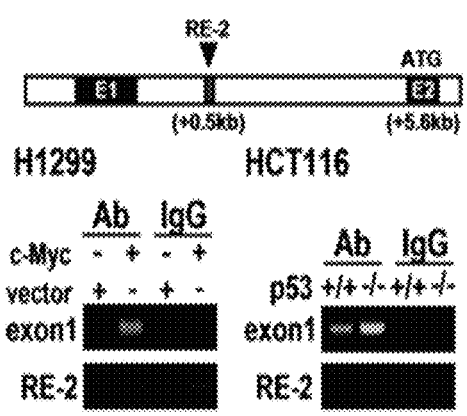

Without being bound by any particular theory, it is believed that Kras and/or c-Myc activation enhances Puf-A expression, as Kras activates Ras/Raf/ERK pathway, which promotes c-Myc binding to Puf-A promoter to induce Puf-A expression in cancer cells, see Example 3 and FIG. 3D.

The present compositions and methods can be used to prevent, treat or inhibit the growth of cancer cells. In some embodiments, methods for preventing or inhibiting cancer cell growth by administering a therapeutic effective amount of Puf-A inhibitor are provided. In an exemplary embodiment, the cancer to be treated or the cancer growth to be inhibited is a cancer expressing Puf-A, selected from colorectal, breast, ovarian, cervical, endometrial, carcinoid, head and neck, thyroid, glioma, lymphoma, lung, melanoma, skin, urothelial, renal, stomach, pancreatic and liver cancers. In another exemplary embodiment, the cancer to be treated or the cancer growth to be inhibited is p-53 deficient cancer, selected from colorectal cancer, lung cancer, breast cancer and glioblastoma.

In other embodiment, methods for preventing lung cancer in a subject with adenoma are provided by administering a therapeutic effective amount of Puf-A inhibitor, wherein the progression of adenoma to adenocarcinoma in the subject is reduced or stopped.

In one embodiment, the Puf-A inhibitor may be administered alone, or as an adjuvant to surgery, e.g., before surgery to reduce the tumor size and/or following surgery to reduce the possibility of metastases, e.g., by inhibition of the growth and migration of circulating tumor cells through the blood stream. In another embodiment, the Puf-A inhibitor can be administered before, after or simultaneously with the anti-cancer agent. In certain instances, the therapy includes a combination of anti-cancer agents to be administered together with the Puf-A inhibitor. The anti-cancer agent includes conventional chemotherapeutic agent, target cancer therapy or radiation therapy.

Puf-A Inhibitor

An Puf-A inhibitor is any agent which reduces or knock down the expression of Puf-A, and/or reduces Puf A's activity.

Puf-A gene expression can be reduced by 0.1-100% by administering a Puf-A inhibitor. For example, the expression may be reduced by 0.5, 1, 5, 10, 15, 20, 25, 30, 35, 40, 45, 50, 55, 60, 65, 70, 75, 80, 85, 90, 95, or even 99%. The expression may be reduced by any amount (%) within those intervals, such as for example, 2-4, 11-14, 16-19, 21-24, 26-29, 31-34, 36-39, 41-44, 46-49, 51-54, 56-59, 61-64, 66-69, 71-74, 76-79, 81-84, 86-89, 91-94, 96, 97, 98 or 99. The gene expression can be measured by methods known in the arts, such as serial analysis of gene expression (SAGE).

In one embodiment, the term "knock-down" refers to a technique of gene silencing in which the expression of Puf-A gene is reduced as compared to the gene expression prior to the introduction of the shRNA or small interfering RNA (siRNA). For example, RNA interference (RNAi), which can involve the use of siRNA, has been successfully applied to knockdown the expression of specific genes in plants, *D. melanogaster, C. elegans*, trypanosomes, planaria, hydra, and several vertebrate species including the mouse and zebrafish. See, for example, U.S. Pat. No. 7,416,849.

In one embodiment, the Puf-A inhibitor is a small molecule. Non limiting examples of Puf-A inhibiting small molecule include a Raf kinase inhibitor, such as Raf (i) (commercially available from Santa Cruz, USA), a MEK inhibitor that inhibits the mitogen-activated protein kinase enzyme (such as PD98059, commercially available from Cell Signaling, USA and UO126, commercially available from Cell Signaling, USA), a stilbene such as resveratrol. In one embodiment, resveratrol is effective to inhibit P53 deficient cancer cells. In another embodiment, resveratrol is effective to inhibit P53 proficient cancer cells.

In some embodiments, the Puf-A inhibitor is an shRNA targeting Puf-A RNA transcription to decrease the expression of Puf-A. In other embodiments, the Puf-A inhibitor is a biosynthetic precursor of a Puf-A-targeted small interfering RNA. In yet another embodiment, the Puf-A inhibitor is any RNA species such as but not limited to, microRNA (miRNA), endoribonuclease-prepared siRNA (esiRNA), natural antisense short interfering RNA (natsiRNA), small interfering RNA (siRNA) wherein the RNA species targets the Puf-A RNA transcription to decrease the expression of NPM.

In one exemplary embodiment, the Puf-A inhibitor is the polynucleotide encoding the shRNA has a nucleotide sequence at least 85, 86, 87, 88, 89, 90, 91, 92, 93, 94, 95, 96, 97, 98, 99 or 100% homologous to SEQ ID NO: 2 or SEQ ID NO: 3. In another exemplary embodiment, the Puf-A inhibitor is the vector disclosed herein.

The Puf-A inhibitor can be administered at any effective amount. In some embodiments, they may be administered at a dose ranging from about 0.01 pg to about 5 g, from about 0.1 µg to about 1 g, from about 1 µg to about 500 mg, from about 10 µg to about 100 mg, from about 50 µg to about 50 mg, from about 100 µg to about 10 mg, from about 0.5 µg to about 5 µg, from about 15 µg to about 500 µg, from about 3 µg to about 1 mg, from about 7 µg to about 1 mg, from about 10 µg to about 20 µg, from 15 µg to about 1 mg, from about 15 µg to about 300 µg, from about 15 µg to about 200 µg, from about 15 µg to about 100 µg, from about 15 µg to about 60 µg, from about 15 µg to about 45 µg, from about 30 µg to about 60 µg, or from about 50 µg to about 100 µg. In certain embodiments, the Puf-A inhibitor is administered in a dose ranging from about 0.1 µg/kg bodyweight to about 200 mg/kg bodyweight, from about 1 µg/kg bodyweight to about 100 mg/kg bodyweight, from about 100 µg/kg to about 50 mg/kg bodyweight, from about 0.5 mg/kg to about 20 mg/kg bodyweight, from about 1 mg/kg to about 10 mg/kg bodyweight, from about 10 µg/kg bodyweight to about 200 µg/kg bodyweight, at least about 0.01 µg/kg bodyweight, about 0.1 µg/kg bodyweight, or at least about 0.5 µg/kg bodyweight.

The dosage of Puf-A inhibitor administered for inhibiting cancer cells will depend on the severity of the condition being treated, the particular formulation, and other clinical factors such as weight and the general condition of the recipient and route of administration.

Useful dosages of the Puf-A inhibitor are determined by comparing their in vitro activity, and in vivo activity in animal models. Methods for the extrapolation of effective dosages in mice, and other animals, to humans are known in the art; for example, see U.S. Pat. No. 4,938,949, which is incorporated by reference herein.

In accordance with the methods provided herein, the Puf-A inhibitor is delivered by any of a variety of routes including, but not limited to, injection (e.g., subcutaneous, intramuscular, intravenous, intra-arterial, intraperitoneal, intradermal); cutaneous; dermal; transdermal; oral(e.g., tablet, pill, liquid medicine, edible film strip); implanted osmotic pumps; suppository, aerosol spray, topical, intra-articular, ocular, nasal inhalation, pulmonary inhalation, impression into skin and vaginal.

The Puf-A inhibitor may be administered in a single dose treatment or in multiple dose treatments, over a period of time appropriate to the condition being treated. The Puf-A inhibitor may conveniently be administered at appropriate intervals, for example, once a day, twice a day, three times a day, once every second day, once every three days or once every week, over a period of at least 3 months or until the symptoms and signs of the condition resolved.

Vector

Some embodiments of the present invention utilize vectors that can be delivered to the cancer cells. As used herein, the term "vector" refers to any viral or non-viral vector, as well as any plasmid, cosmid, phage or binary vector in double or single stranded linear or circular form that may or may not be self-transmissible or mobilizable, and that can transform prokaryotic or eukaryotic host cells either by integration into the cellular genome or which can exist extrachromosomally (e.g., autonomous replicating plasmid with an origin of replication). Any vector known in the art is envisioned for use in the practice of this invention.

Non limiting examples of viral vector include adeno-associated viral vector, lentivirus vector, adenoviral vector, polioviral vector, herpes simplex viral vector, or murine-based viral vector. Non limiting examples of non-viral vector include a DNA vector (encoding a desired sequence can be introduced in vivo by lipofection), synthetic cationic lipids (liposomes for in vivo transfection of a gene encoding a marker (Feigner, et al. (1987) Proc. Natl. Acad. Sci. USA 84:7413-7); see Mackey, et al. (1988) Proc. Natl. Acad. Sci. USA 85:8027-31; Ulmer, et al. (1993) Science 259:1745-8). Particularly useful lipid compounds and compositions for transfer of nucleic acids are described in International Patent Publications WO 95/18863 and WO 96/17823, and in U.S. Pat. No. 5,459,127. Lipids may be chemically coupled to other molecules for the purpose of targeting. Targeted peptides, for example, hormones or neurotransmitters, and proteins, for example, antibodies, or non-peptide molecules could be coupled to liposomes chemically. Other molecules are also useful for facilitating transfection of a nucleic acid in vivo, for example, a cationic oligopeptide (for example, International Patent Publication WO 95/21931), peptides derived from DNA binding proteins (for example, International Patent Publication WO 96/25508), or a cationic polymer (for example, International Patent Publication WO 95/21931).

The viral vector according to the invention are generally formulated and administered in the form of doses of between about $10^4$ and about $10^{14}$ pfu. In the case of AAVs and adenoviruses, doses of from about $10^6$ to about $10^{11}$ pfu are particularly used. The term pfu ("plaque-forming unit") corresponds to the infective power of a suspension of virions and is determined by infecting an appropriate cell culture and measuring the number of plaques formed. The techniques for determining the pfu titer of a viral solution are well documented in the art.

The vector of the present invention comprises a polynucleotide encoding an shRNA, having a nucleotide sequence at least 85, 86, 87, 88, 89, 90, 91, 92, 93, 94, 95, 96, 97, 98, 99 or 100% homology to SEQ ID NOs: 2 and 3. The polypeptide may be operably linked to one or more promoters.

In one embodiment, the promoter is a nucleotide sequence, usually upstream (5') to its coding sequence, which directs and/or controls the expression of the coding sequence by providing the recognition for RNA polymerase and other factors required for proper transcription. In one exemplary embodiment, promoter includes a minimal promoter that is a short DNA sequence comprised of a TATA-box and other sequences that serve to specify the site of transcription initiation, to which regulatory elements are added for control of expression. In another embodiment, promoter is a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. In some embodiments, an enhancer is a DNA sequence that stimulates promoter activity and may be an innate element of the promoter or a heterologous element inserted to enhance the level or tissue specificity of a promoter. It is capable of operating in both orientations (sense or antisense), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Any promoter known in the art which regulates the expression of the shRNA or RNA coding sequence is envisioned in the practice of the invention.

ShRNA can be delivered into mammalian cells, particularly human cells, by a gene therapy approach, using a DNA vector from which shRNA can be transcribed directly. The production of such shRNAs can be readily achieved in vivo by transfecting cells or tissues with DNA vectors bearing short inverted repeats separated by a small number of (e.g., 3, 4, 5, 6, 7, 8, 9) nucleotides that direct the transcription of such small hairpin RNAs. Additionally, if mechanisms are included to direct the integration of the vector or a vector segment into the host-cell genome, or to ensure the stability of the transcription vector, the RNAi caused by the encoded shRNAs, can be made stable and heritable. Not only have such techniques been used to "knock down" the expression of specific genes in mammalian cells, but they have now been successfully employed to knock down the expression of exogenously expressed transgenes, as well as endogenous genes in the brain and liver of living mice.

Pharmaceutical Composition

Some embodiments of the present invention are directed to pharmaceutical compositions comprising a vector described herein and a pharmaceutically acceptable carrier.

The term "pharmaceutically acceptable carrier" is a carrier that is compatible with the other ingredients of the formulation, and not deleterious to the recipient thereof. The active ingredient for administration may be present as a powder or as granules; as a solution, a suspension or an emulsion or as described elsewhere throughout the specification.

In one embodiment, pharmaceutical compositions are prepared by uniformly and intimately bringing into association active components of the pharmaceutical compositions (e.g., a vector) with liquid carriers, with solid carriers, or with both. Liquid carriers include, but are not limited to, aqueous formulations, non-aqueous formulations, or both. Solid carriers include, but are not limited to, biological carriers, chemical carriers, or both.

The pharmaceutical compositions are administered in an aqueous suspension, an oil emulsion, water in oil emulsion and water-in-oil-in-water emulsion, and in carriers including, but not limited to, creams, gels, liposomes (neutral, anionic or cationic), lipid nanospheres or microspheres, neutral, anionic or cationic polymeric nanoparticles or microparticles, site-specific emulsions, long-residence emulsions, sticky-emulsions, micro-emulsions, nano-emulsions, microspheres, nanospheres, nanoparticles and minipumps, and with various natural or synthetic polymers that allow for sustained release of the pharmaceutical composition including anionic, neutral or cationic polysaccharides and anionic, neutral cationic polymers or copolymers, the minipumps or polymers being implanted in the vicinity of where composition delivery is required. Furthermore, the active components of the pharmaceutical compositions provided herein are useful with any one, or any combination of, carriers. These include, but are not limited to, anti-oxidants, buffers, and bacteriostatic agents, and optionally include suspending agents, thickening agents or preservatives.

The following examples further illustrate the present invention. These examples are intended merely to be illustrative of the present invention and are not to be construed as being limiting.

EXAMPLE 1

Expression of Puf-A in Various Cancers

The expression of Puf-A was evaluated 20 types of cancer using immunohistochemical staining. Puf-A expression was medium to high in colorectal, breast, ovarian, cervical, endometrial, carcinoid, head and neck, thyroid, glioma, lymphoma, lung, melanoma, skin, urothelial, renal, stomach, pancreatic and liver cancers. See FIG. 1A.

Figure 1B:
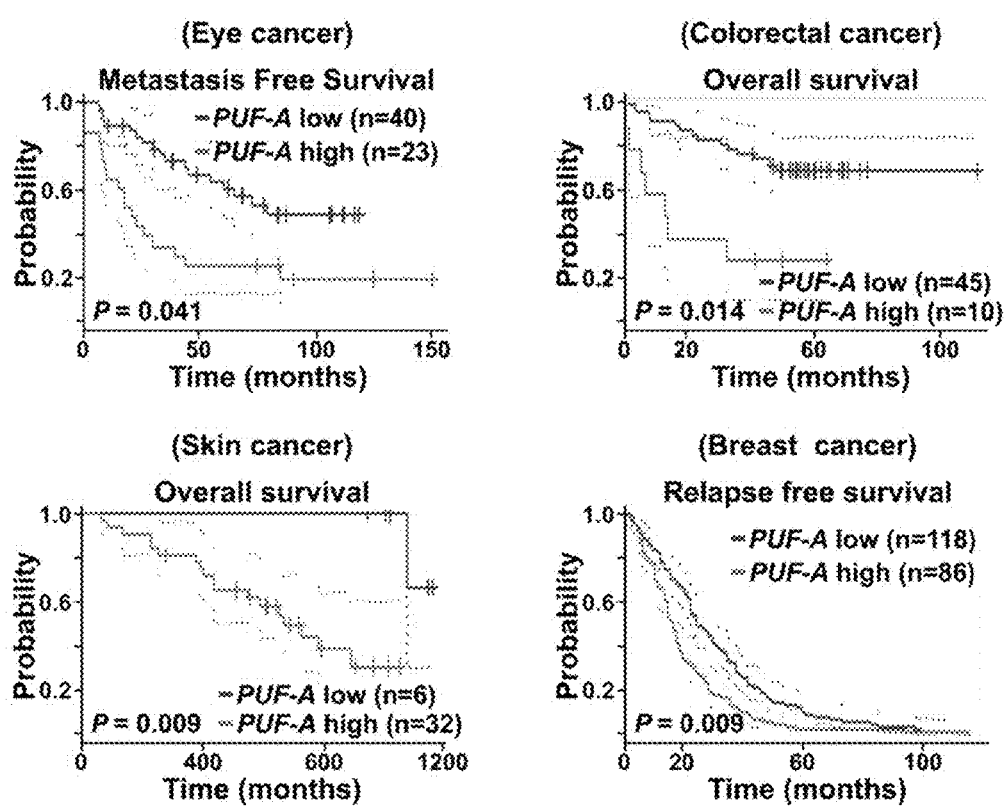
FIG. 1B is an assembly of graphs illustrating a higher Puf-A expression is correlated with a shorter overall survival rate in eye caner, colorectal cancer, skin cancer and breast cancer.

FIG. 1B is an assembly of Kaplan-Meier analyses of patients' overall survival and Puf-A expression in eye, colorectal, skin and breast cancers. A higher Puf-A expression (red line) is correlated with a shorter overall survival in patients with eye, colorectal, skin and breast cancer.

EXAMPLE 2

Expression of Puf-A in Advanced Human Lung Adenocarcinomas

Figure 2A:
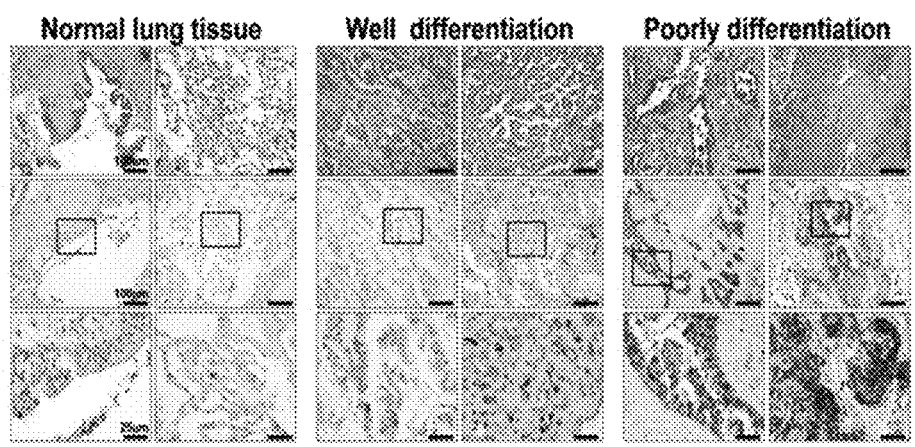
FIG. 2A is an assembly of immunohistochemical images showing the expression of Puf-A in normal lung cells, well differentiated lung adenocarcinoma cells and poorly differentiated lung adenocarcinoma cells.

The expression of Puf-A was examined using antibodies directed against Puf-A in normal lung tissue, well differentiated and poorly differentiated lung adenocarcinoma. The result shows Puf-A expression was higher in lung adenocarcinoma compared to normal lung tissue, and is related to the degree of differentiation (i.e., highest Puf-A in poorly differentiated adenocarcinoma), as illustrated in FIG. 2A.

Figure 2B:
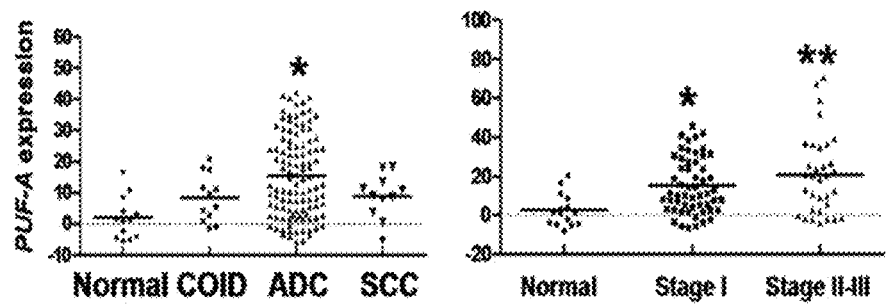
FIG. 2B is a series of graphs illustrating Puf-A RNA level in carcinoid tumors (COID), adenocarcinomas of the lung (ADC), squamous cell carcinomas of the lung (SCC), small-cell lung cancer (SCLC), and normal lung sample (left graph), and Puf-A RNA level in different stages of human lung adenocarcinomas (right graph).

The expression of Puf-A RNA expression was evaluated in 126 patients with lung cancer, based on the data obtained from an independent source http://www.genome.wi.mit.edu/MPR/lung (PNAS, 98: 13790-13795 2001). Of the 126 patients, 10 had carcinoid tumors (COID), 109 had adenocarcinomas (ADC), 11 had squamous cell carcinomas (SCC) and 6 had small-cell lung cancer (SCLC), and 13 non-neoplastic lung samples were used as control (Normal). Referring to FIG. 2B (left panel), all of the lung cancers expressed more Puf-A RNA compared to the Normal, with ADC expressed the highest level of Puf-A RNA (7.8-fold) compared to the Normal. The expression of Puf-A RNA at different stages of ADC was analyzed in 55 patients with stage I and 22 patients with stage ADC, as well as 15 non-neoplastic lung samples (Normal). FIG. 2B (right panel) shows the expression of Puf-A RNA in Stage I and stage AD are 5.9- and 12.0-folds, respectively, compared to Normal.

Figure 2C:
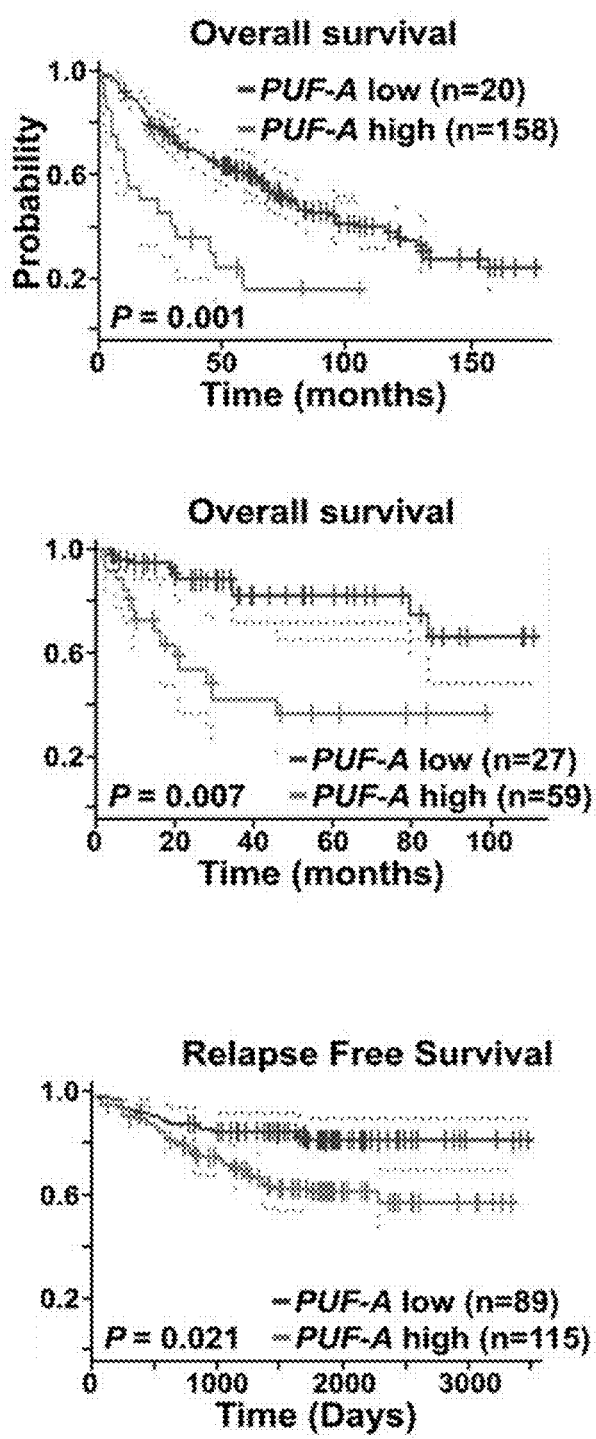
FIG. 2C is a series of graphs illustrating relationship between the expressions of Puf-A RNA and the survival rates of patients with adenocarcinoma of the lung.

Kaplan-Meier analysis shows a higher Puf-A expression in ADC (red line) is correlated with a shorter survival (overall survival or relapse free survival) of patients, compare to a lower Puf-A expression (blue line) (FIG. 2C).

EXAMPLE 3

In Vitro Evaluation of Kras Activation on Puf-A Expression

An in vitro evaluation of the effect of Kras activation on Puf-A expression was performed using $Kras^{G12D}$ transduced and control vector transduced H1299 lung cancer cells. The expression levels of Puf-A protein and RNA were analyzed by western blot and qPCR.

As shown in FIG. 3A, the expression levels of Puf-A protein and RNA in the Kras$^{G12D}$ transduced lung cancer cells increased by 2- and 1.5-fold respectively, compared to that of control vector transduced lung cancer cells. The expression levels of c-Myc protein and RNA in the Kras$^{G12D}$ transduced lung cancer cells increased by 1.8- and 1.4-fold respectively, compared to that of control vector transduced cells.

Since Kras signaling is involved in the induction of c-Myc expression and could activate c-Myc expression (Nature 475: 106-109, 2011), the effect of c-Myc activation on Puf-A expression was evaluated using H1299 lung cancer cells, infected with c-Myc or vector control virus. The expression levels of Puf-A protein and RNA in the c-Myc transduced cells respectively increased by 2.5- and 1.7-fold compared to vector control transduced cells (FIG. 3B).

In addition, the Puf-A promoter activity was examined in cells transfected with Kras$^{G12D}$ or c-Myc expression plasmids. It was found that the Kras$^{G12D}$ and c-Myc increased Puf-A promoter activity by 2.2- and 3.2-fold respectively, compared to the control vector (FIG. 3C), suggesting that c-Myc might involve in transcriptional control of Puf-A gene expression. In addition, there was more endogenous c-Myc protein in p53$^{-/-}$ HCT116 cancer cells compare to p53$^{+/+}$ HCT116 cancer cells (data not show).

To confirm that c-Myc is involved in transcriptional control of Puf-A gene expression, H1299 cells were infected with c-Myc or vector control lenti-virus and chromatin immuno-precipitation (CHIP) assay was used to examine the location of c-Myc consensuses sequence in Puf-A promoter. The results showed that the exogenous c-Myc protein bind on the c-Myc consensuses sequence in exon 1 of Puf-A locus and there was more c-Myc protein binding to exon1 of Puf-A locus in p53$^{-/-}$ HCT116 cells than in that p53$^{+/+}$ cells, indicating that c-Myc induced Puf-A gene expression was mediated through c-Myc binding to the Puf-A promoter. (FIG. 3D).

Figure 3E:
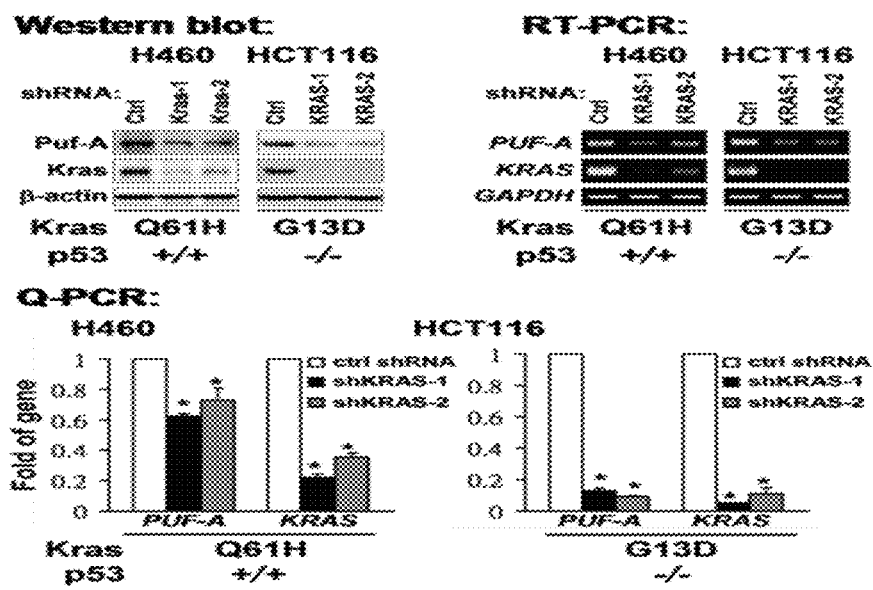

The data in FIG. 3A shows that Kras signaling is essential for Puf-A gene expression, two cancer cell lines harboring oncogenic Kras, including H460 lung cancer and HCT116 colorectal cancer cells were used to examined the effect of Kras depletion in Puf-A expression. After the depletion of Kras using shKras, Puf-A protein and RNA were significantly reduced compared to control shRNA transduced cells (FIG. 3E).

Figure 3F:
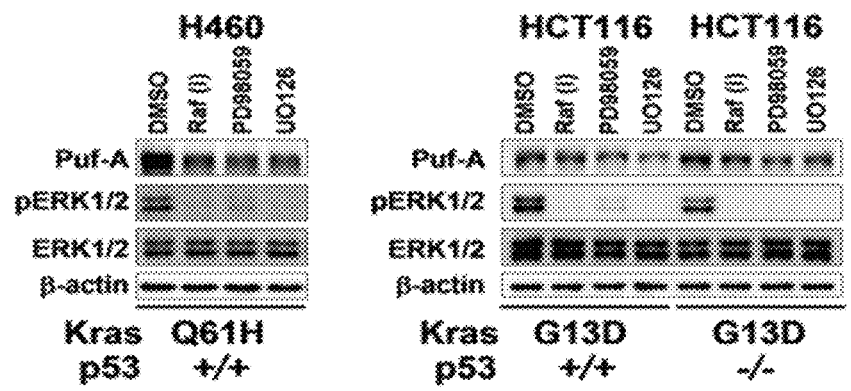

The effect of various small molecules (such as Raf(i), PD98059 and UO126), which block the downstream effectors of Kras pathway (such as Rafs, MEK1 and MEK2), was assessed in H460 and HCT116 cancer cells. FIG. 3F shows the expression levels of Puf-A was reduced after the administration of small molecules to block the downstream effectors of Kras pathway.

EXAMPLE 4

The Effect of Oncogenic Kras Activation on Puf-A Expression.

The expression of Puf-A was evaluated using CCSP-rtTA/TetO-Cre/LSL-Kras$^{G12D}$p53$^{+/+}$ mice with Kras$^{G12D}$ induced lung adenocarcinoma. The bronchiolar Clara cells were identified as the origin of cells for Kras induced neoplasia in the lungs (H C Cho et al., Identification of Tumorigenic Cells in Kras$^{G12D}$-Induced Lung Adenocarcinoma, Cancer Res. 2011, 71: 7250-7258).

Figure 4A:
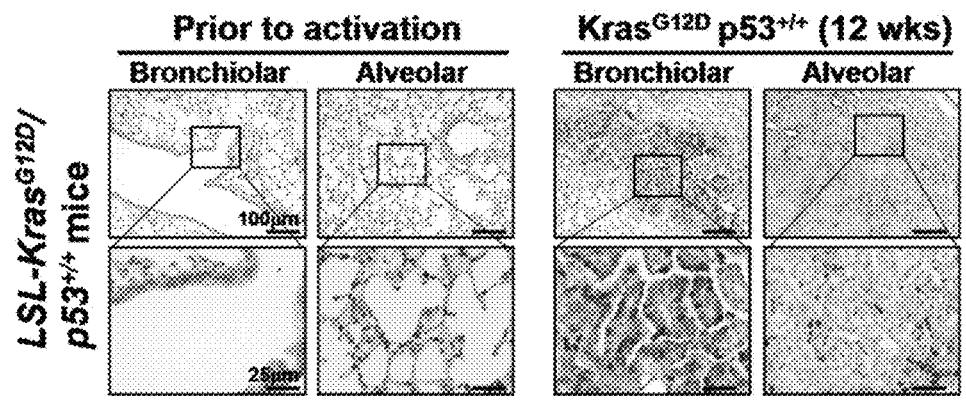
FIG. 4A is an assembly of images illustrating the immunohistochemical staining of Puf-A in the bronchiolar and alveolar cells in mice, prior to $Kras^{G12D}$ activation (left panel) and after 12 weeks of $Kras^{G12D}$ activation (right panel).

In normal mice prior to Kras$^{G12D}$ activation, both bronchiolar and alveolar epitheliums were weakly positive for Puf-A staining (FIG. 4A, left panel). After 12 weeks of Kras$^{G12D}$ activation, the lung cancer tissue of the mice (CCSP-rtTA/TetO-Cre/LSL-Kras$^{G12D}$p53$^{+/+}$) show a significant increase in Puf-A positive bronchiolar cells, whereas there were only a few Puf-A positive alveolar cells (FIG. 4A, right panel).

Figure 4B:
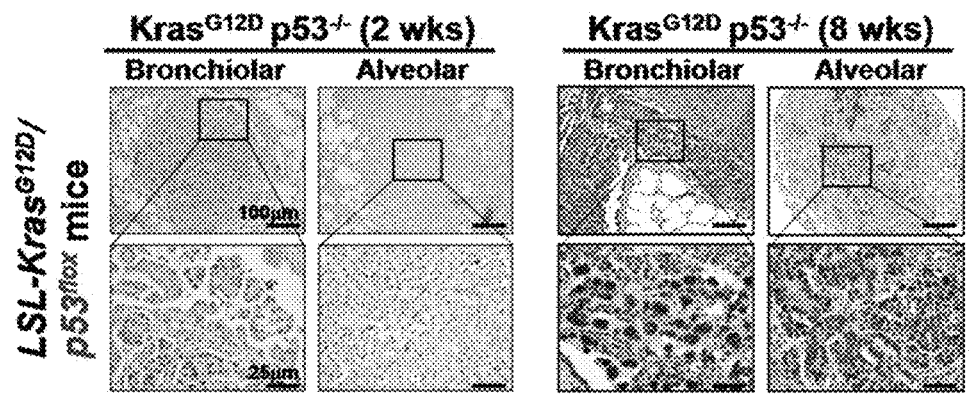
FIG. 4B shows the immunohistochemical staining of Puf-A in the bronchiolar and alveolar cells in mice after 2 weeks (left panel) and 8 weeks (right panel) of $Kras^{G12D}$ activation and p53 deletion.

FIG. 4B (left panel) and FIG. 4B (right panel) show 2 weeks and 8 weeks of Kras$^{G12D}$ activation and p53 deletion in CCSP-rtTA/TetO-Cre/LSL-Kras$^{G12D}$1p53$^{flox}$ mice, respectively. After 2 weeks of Kras$^{G12D}$ activation and p53 deletion, more Puf-A positive cells were seen in the bronchiolar epithelium compare to that in the alveolar epithelium (FIG. 4B, left panel). The intensity of Puf-A staining in both bronchiolar and alveolar epitheliums further increased after 8 weeks after Kras$^{G12D}$ activation and p53 deletion, more in the bronchial epithelium (FIG. 4B, right panel). These results suggest Puf-A expression is correlated with oncogenic Kras activation and/or p53 depletion.

EXAMPLE 5

The Effect of Puf-A Suppression in Tumourigenesis

An in vivo evaluation of Puf-A suppression in tumourigenesis was performed using LSL-Kras$^{G12D}$1p53$^{flox}$ mice.

Figure 5A:
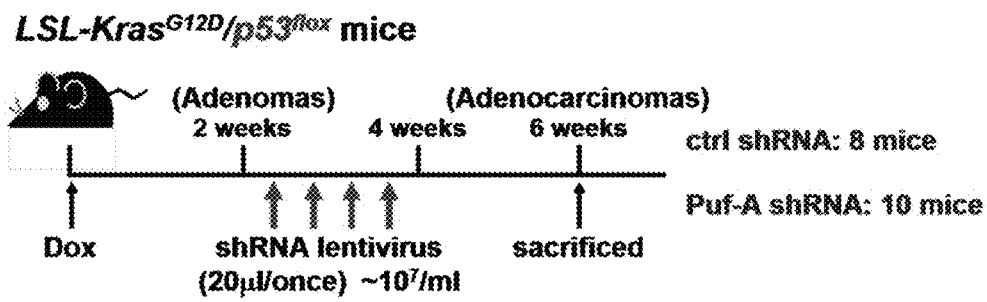
FIG. 5A schematically illustrates the in vivo study design of Puf-A shRNA delivery to knock down Puf-A.
Figure 5B:
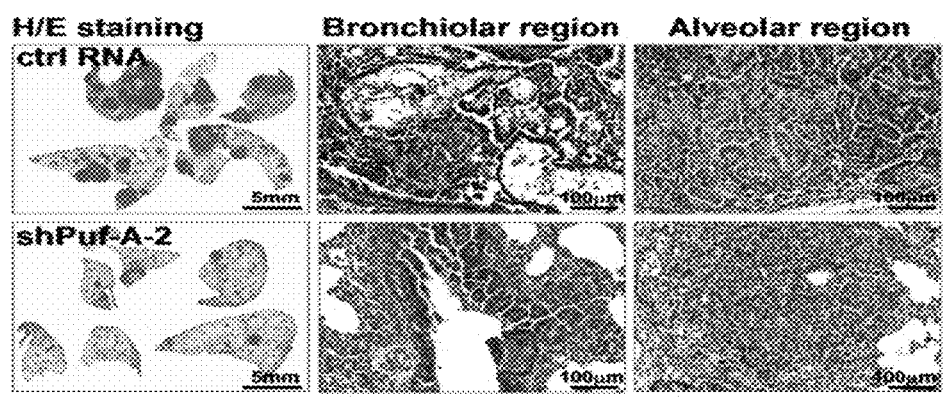
FIG. 5B is an assembly of microscopic images illustrating the number of tumor foci in mice administered with of control shRNA or Puf-A shRNA.
Figure 5C:
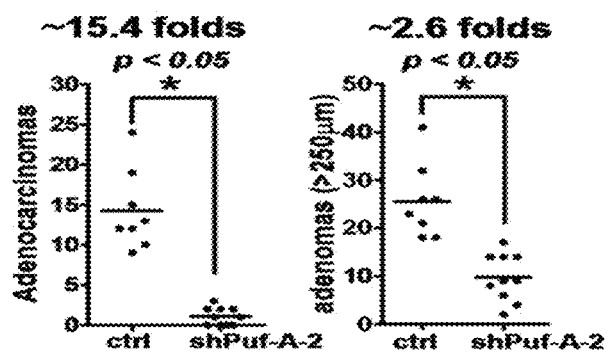
FIG. 5C is a series of bar graphs illustrating the counted numbers of tumor foci (>250 μm) in mice with adenocarcinoma (left bar graph) and adenoma (right bar graph), after the administration of control or Puf-A-2 shRNA.

FIG. 5A schematically illustrates the study design. LSL-Kras$^{G12D}$/p53$^{flox}$ mice developed adenoma after 2 weeks of Kras$^{G12D}$ activation and p53 deletion. Lentiviral vector, expressing shPuf-A-2 (a Puf-A shRNA) or control shRNA, was intranasally delivered to adenoma-bearing LSL-Kras$^{G12D}$/p53$^{flox}$ mice twice a week for two weeks. The mice were sacrificed 6 weeks after Kras$^{G12D}$ activation and p53 deletion. The lung tissues were examined and showed less adenocarcinoma foci in the bronchiolar and alveolar regions of lungs in mice treated with shPuf-A-2 lentiviral vector compared to the control vector, as illustrated in FIG. 5B. The number of adenocarcinoma or adenoma focus (>250 μm) in mice treated with shPuf-A-2 lentiviral vector was significantly less (15.4 and 2.6-fold reduction, respectively) than that in mice transfected with control shRNA vector (FIG. 5C). These results suggest that Puf-A is effective in suppressing lung tumorigenesis, and preventing the progression of lung adenoma to lung adenocarcinoma.

EXAMPLE 6

Effect of Novel shPuf-A on Puf-A Expression

FIG. 6B shows the nucleotide sequences of the polypeptide encoding two novel short hairpin RNAs, shPuf-A-1 (SEQ ID NO:2) and shPuf-A2 (SEQ ID NO:3).

The effect of the shRNAs constructs in FIG. 6B on Puf-A expression was evaluated using p53-proficient (p53$^{+/+}$ HCT116) and p53-deficient (p53$^{-/-}$ HCT116 and p53$^{-/-}$ H1299). The cells were transduced with control shRNA, shPuf-A-1 and shPuf-A-2 lentivirus vectors and Puf-A expression was determined by real-time quantitative PCR and Q-PCR. FIG. 6C and FIG. 6D show in both p53-proficient and p53-deficient cancer cells transfected with shPuf-A-1 and shPuf-A-2 lentiviral vectors, the expression level of Puf-A RNA is significantly reduced compared to that of control shRNA (GAPDH was used as internal control). The knockdown efficiencies of shPuf-A-1 and shPuf-A-2 on Puf-A expression were approximately 90% and 75%, respectively, compare to the control shRNA (FIG. 6D).

EXAMPLE 7

Effect of Silencing Puf-A on Cancer Cells

The biological function of Puf-A on cancer cells was assessed, using lung cancer cells (A549, H460, H1299 and CL1-5); colorectal cancer cells (HCT116); breast cancer cells (MB231) and glioblastoma cells (U87, LN229 and T98). These cancer cell lines were transfected with the Puf-A-1 and Puf-A-2 virus vectors in Example 6, which significantly reduced the expression level of Puf-A proteins compared to that of control shRNA. In addition, shPuf-A transduction significantly increased the cleaved form of Poly ADP-ribose polymerase 1 (PARP1) in p53-deficient cells ($p53^{-/-}$ HCT116, $p53^{-/-}$ H1299, $p53^{R248W}$ C.L1-5 and $p53^{R280K}$ MB231) compared to control shRNA transduction. In p53-proficient cancer cells ($p53^{+/+}$ A549, H460 and HCT116), Puf-A depletion did not affect the level of cleaved PARP1 (FIG. 7A).

Figure 7A:
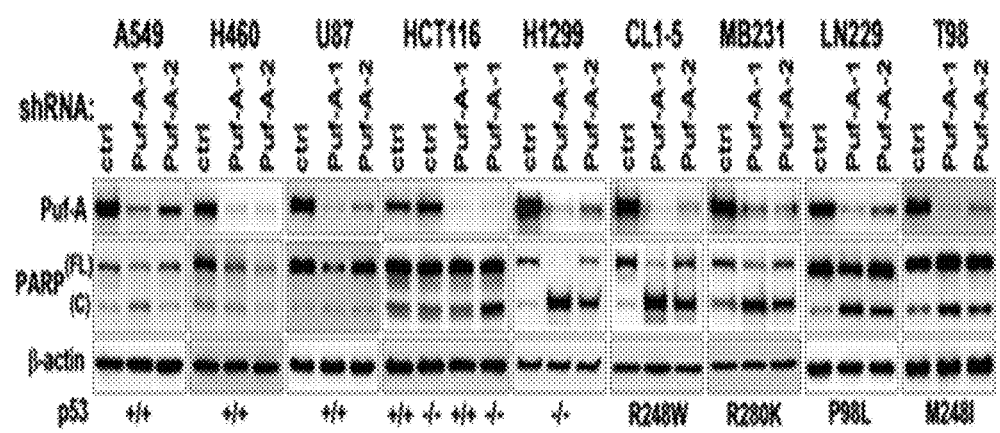
FIG. 7A is an assembly of images showing the effect of control shRNA, shPuf-A-1 and Puf-A-2 on Puf-A expression and cleaved form of PARP1, by transducing control shRNA, shPuf-A-1 and Puf-A-2 into the following p53-deficient and p53-proficient cell lines: A549, H460, U87, HCT116, H1299, CL1-5, MB231, LN229 and T98.
Figure 7B:
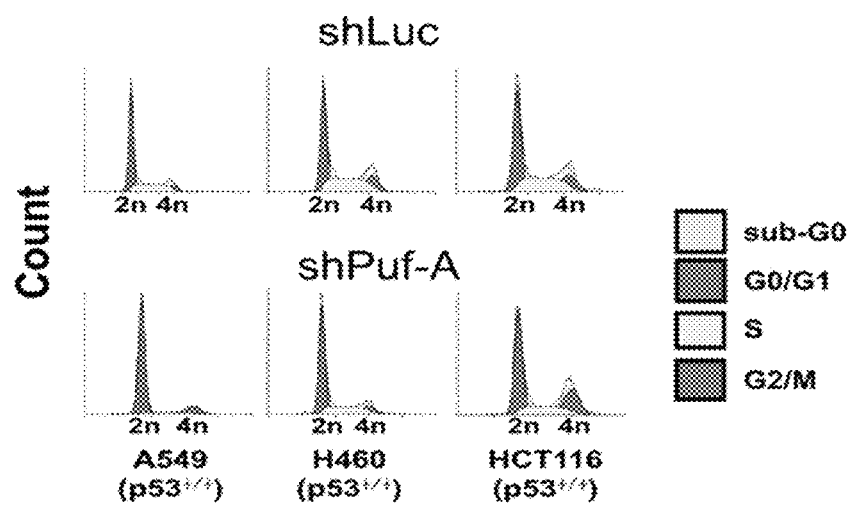
FIG. 7B is a series of flow cytometry (FACS) images, illustrating the cell-cycle of Puf-A depleted (shPuf-A transduced) p53 proficient (p53 wild type) and p53 deficient (p53 defective) cancer cell lines.
Figure 7B:
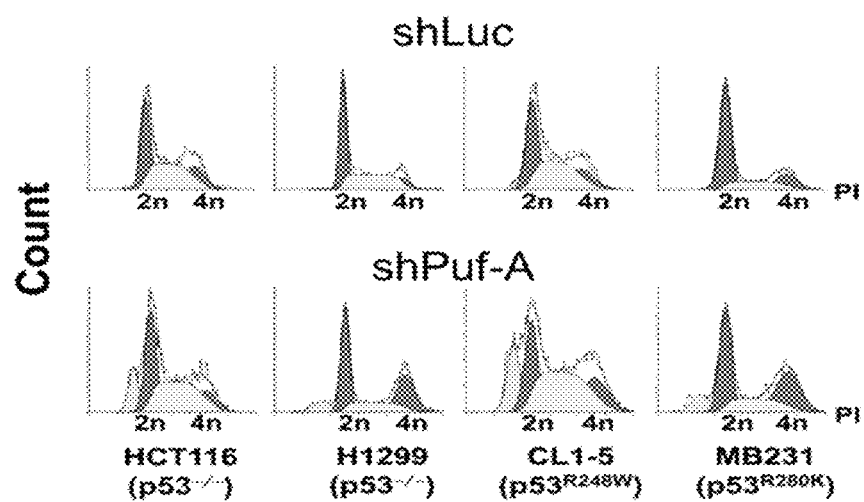

Referring to FIG. 7B, the cancer cell lines in FIG. 7A were transduced with shPuf-A virus vectors, followed by the incubation with propidium iodide (PI) to assess DNA-based cell-cycle distribution, using FACS. The sub-G1 cell population (blue) in p53-deficient cancer cells ($p53^{-/-}$ H1299 and HCT116) after shPuf-A transduction with a virus vector increased significantly compared to that of the control shRNA group. This result is consistent with the increased level of cleaved PARP1 after depletion of Puf-A in p53-deficient cancer cells (see FIG. 7A), suggesting the depletion of Puf-A in p53-deficient cancer cells leads to cell death.

Figure 7C:
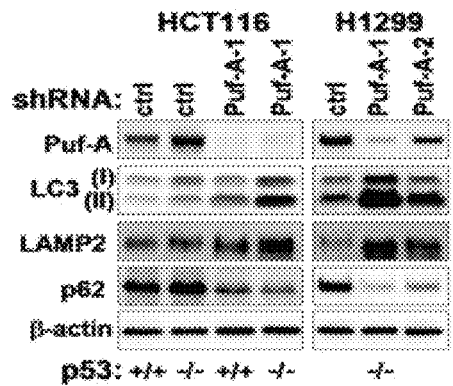
FIG. 7C is a series of Western blot images showing the effect shPuf-A-1 transduction on the expression of Puf-A, LC3 (marker for autophagosome), LAMP2 (marker for lysosome) and p62 (an autophagy substrate) in $p53^{+/+}$HCT116, $p53^{-/-}$HCT116, and $p53^{-/-}$H1299 cancer cell lines.

It has been reported that the loss of p53, in response to various stimuli, increases autophagic flux and LC3 accumulation and leads to cell death (PNAS, 107: 18511-18516, 2010). Western blot images of FIG. 7C show the expression levels of LC3-II (component of autophagosome) and LAMP2 (component of lysosome) increased significantly in p53-deficient cancer cells ($p53^{-/-}$ HCT116 and H1299 cells) after shPuf-A transduction, whereas p62 (a substrate of enzyme digestion with the formation of autolysosomes in the cells) was degraded and its expression level significantly reduced in the same Puf-A silenced p53-deficient cancer cells. These results suggest p53-deficient cancer cells undergo autophagic cell death after the transduction of shPuf-A vector.

Figure 7D:
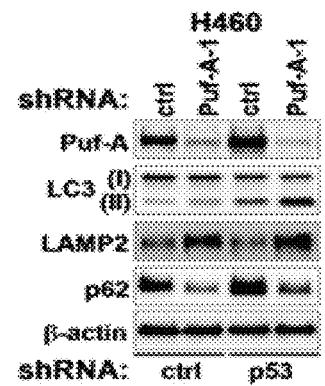
FIG. 7D is a Western Blot image illustrating the effect of suppressing p53 and Puf-A in p53-proficient cells (H460).

Depletion of Puf-A in p53-proficient cells ($p53^{+/+}$ HCT116), after shPuf-A-1 and shPuf-A-2 transduction, led to a slight increase in the level of LC3-II expression, compared to p53-deficient cells (FIG. 7C). However, simultaneous depletion of p53 and Puf-A in p53-proficient cells ($p53^{+/+}$ H460) led to a significant increase in LC3-II and LAMP2 expression (FIG. 7D), compared to Puf-A depletion only (FIGS. 7C and 7D).

Figure 7E:
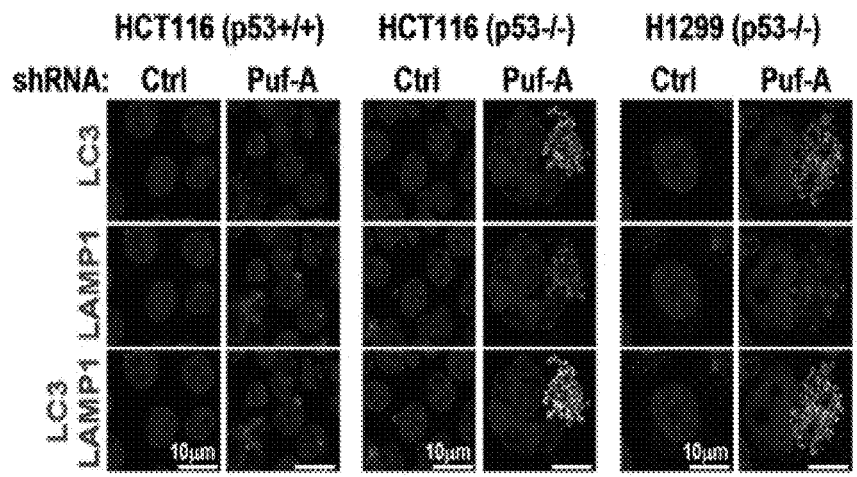
FIG. 7E is a series of immunofluorescence images illustrating the effect of silencing Puf-A, by shPuf-A-1 transduction, on LC3 (green), Lamp1 (red) and DAPI (blue) expression in p53 proficient ($p53^{+/+}$) HCT116, P53 deficient ($p53^{-/-}$) HCT116 and H1299 cancer cells.

The immunofluorescence staining in FIG. 7E show an increase expression and co-localization of LC3-II (green) and LAMP1 (red) in p53-deficient cancer cells after shPuf-A-1 vector transduction, compared to a slight increase of LAMP1 around the nuclei in p53-proficient cancer cells. This suggest aberrant autolysosome formation in p53 deficient cancer cells, as depletion of Puf-A lead to increased autophagic flux, aberrant LC3-II accumulation and autophagic cell death.

Figure 7F:
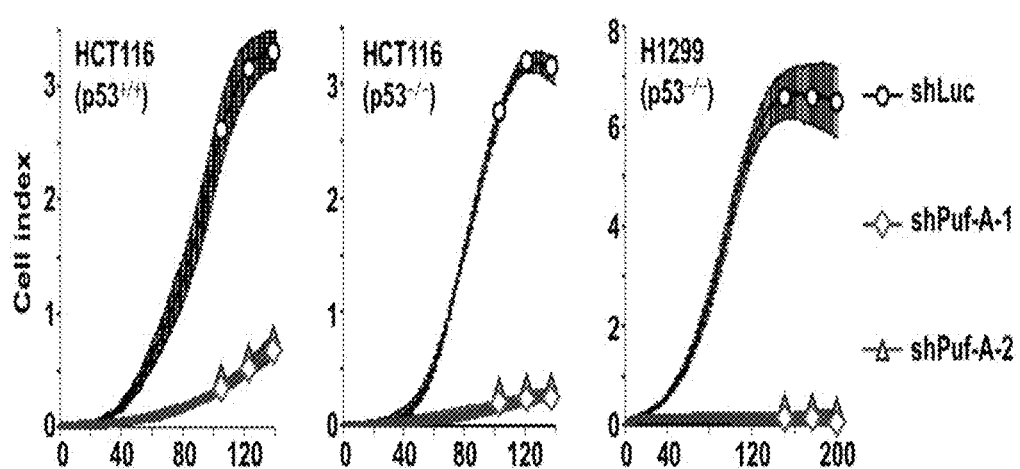
FIG. 7F is a series of graphs illustrating reduced proliferation rate of $p53^{-/-}$ HCT116 and H1299 cells after shPuf-A-1 and shPuf-A-2 transduction compared to control shRNA transduction.

The proliferation rate of p53-deficient and P53-proficient cancer cells was reduced after the transduction of shPuf-A-1 and shPuf-A-2, compared to the same cancer cells transduced with control shRNA virus (FIG. 7F). These results indicate that Puf-A suppression induces autophagic cell death in cancer cells, more prominent in p53-deficient cells.

EXAMPLE 8

Effect of Puf-A Suppression in p53 Proficient Cancer Cells

Figure 8A:
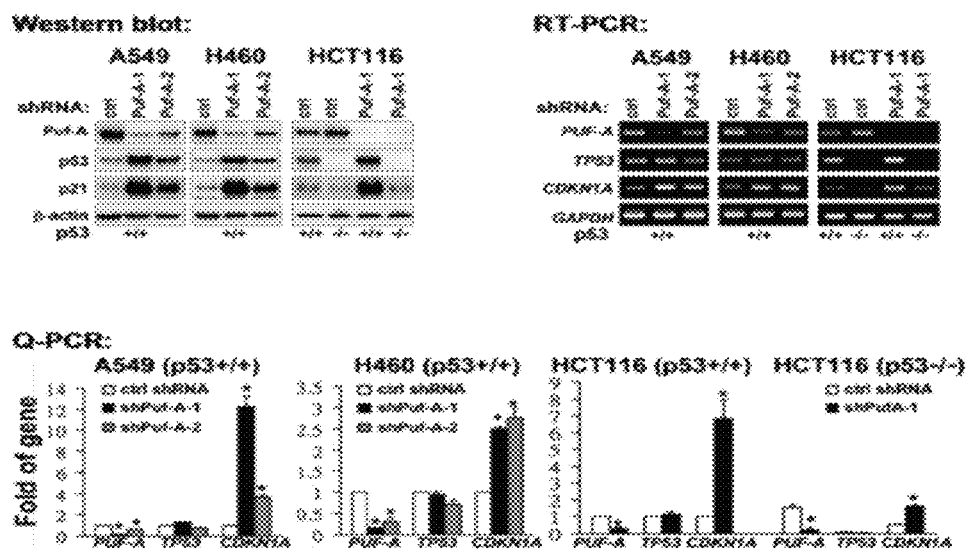
FIG. 8A is a series of Western blot, RT-PCR and Q-PCR images, illustrating shPuf-A1 and shPuf-A2 transduction increases the expression of p53 and p21 and reduces transcripts of PUF-A in the following p53-proficient ($p53^{+/+}$) cancer cell lines: A549, H460, and HCT116.
Figure 8B:
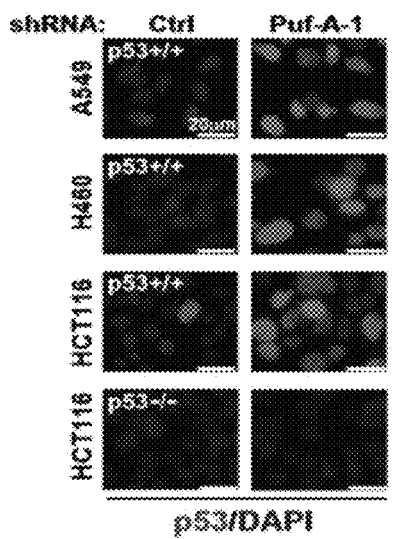
FIG. 8B is a series of immunostaining images illustrating the expression of p53 (red) and DAPI (blue, internal control) in p53-proficient ($p53^{+/+}$) cancer cell lines A549, H460 and HCT116 cells and P53 deficient ($p53^{-/-}$) HCT116 cancer cells after control shRNA and shPuf-A-1 transduction.
Figure 8C:
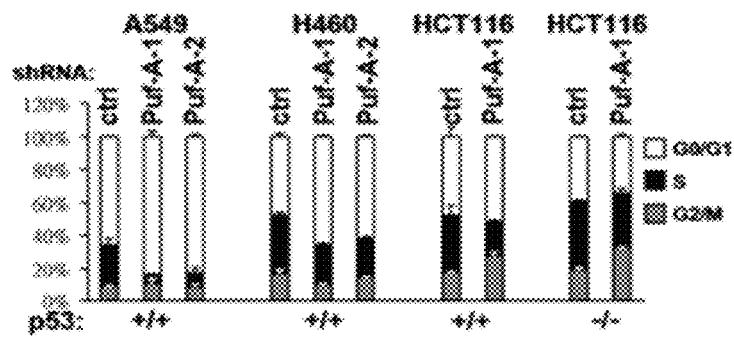
FIG. 8C is a series of bar graphs illustrating the FACS analyzed cell-cycles of Puf-A depleted cancer cells, A549, H460 and HCT116, with different p53 genotypes.
Figure 8D:
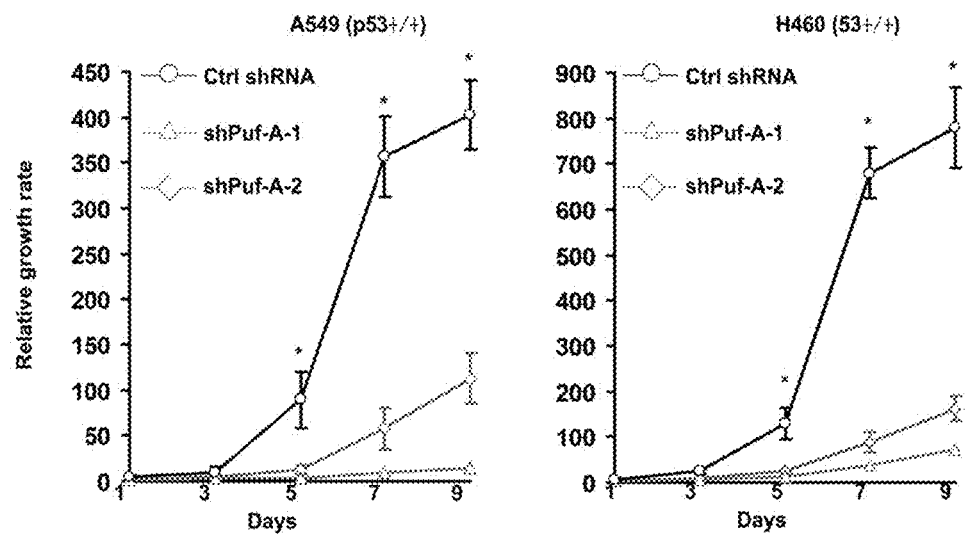
FIG. 8D are two graphs showing the depletion of Puf-A significantly reduced the proliferation rate of p53-proficient ($p53^{+/+}$) A549 and H460 cells.

The effect of Puf-A suppression on the expression level of p53 and p21 protein/RNA in p53 proficient cancer cells was examined, by infecting A549, H460 or HCT116 cancer cells with shPuf-A-1, shPuf-A-2 or control shRNA viral vectors. FIG. 8A shows the expression levels of p53 and p21 protein or RNA significantly increased in p53 proficient cancer cells compared to cancer cells infected with control shRNA. Similar findings were seen in immunofluorescence staining, with increased p53 nuclear staining (red) in p53-proficient cells after depletion of Puf-A (FIG. 8B). Cell-cycle progression of the same cancer cell lines was analyzed by FACS. As illustrated in FIG. 8C, the S-phase cell population significantly reduced, whereas the G0/G1-phase cell population increased in p53-proficient cancer cells after shPuf-A transduction. FIG. 8D illustrates the growth rate of p53-proficient A549 and H460 cancer cells significantly decreased after Puf-A depletion. These results suggest by silencing Puf-A expression in p53 proficient cancer cells, p53 and p21 expression increased, which in term lead to cell cycle arrest in p53-proficient cells.

EXAMPLE 9

Effect of Puf-A Suppression on Hepatoma Cells

The effect of Puf-A suppression on hepatoma cells is assessed. P53 proficient ($p53^{+/+}$ HepG2) and p53 deficient ($p53^{-/-}$ Hep3B and p53Y220C Huh-7) hepatoma cells are infected with Puf-A shRNA or control shRNA.

The expression of Puf-A is reduced and cell death is increased in p53 proficient and p53 deficient hepatoma cells infected with Puf-A shRNA, in comparison with the control group.

EXAMPLE 10

Figure 9A:
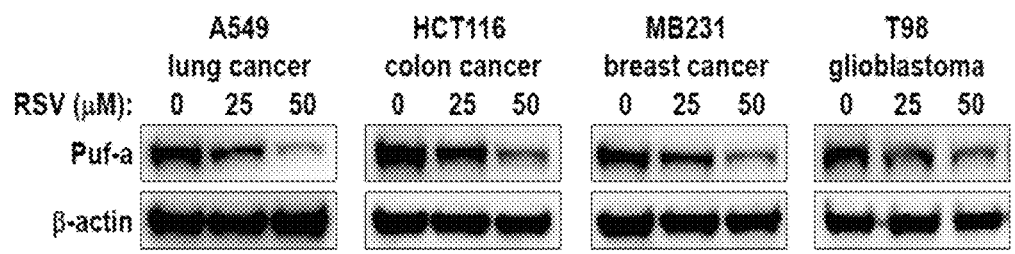
FIG. 9A is an assembly of Western blot images illustrating 25 and 50 uM of resveratrol reduced the expression of Puf-a in A549 lung cancer cells, HCT116 colon cancer cells, MB231 breast cancer cells and T98 glioblatoma cells.
Figure 9B:
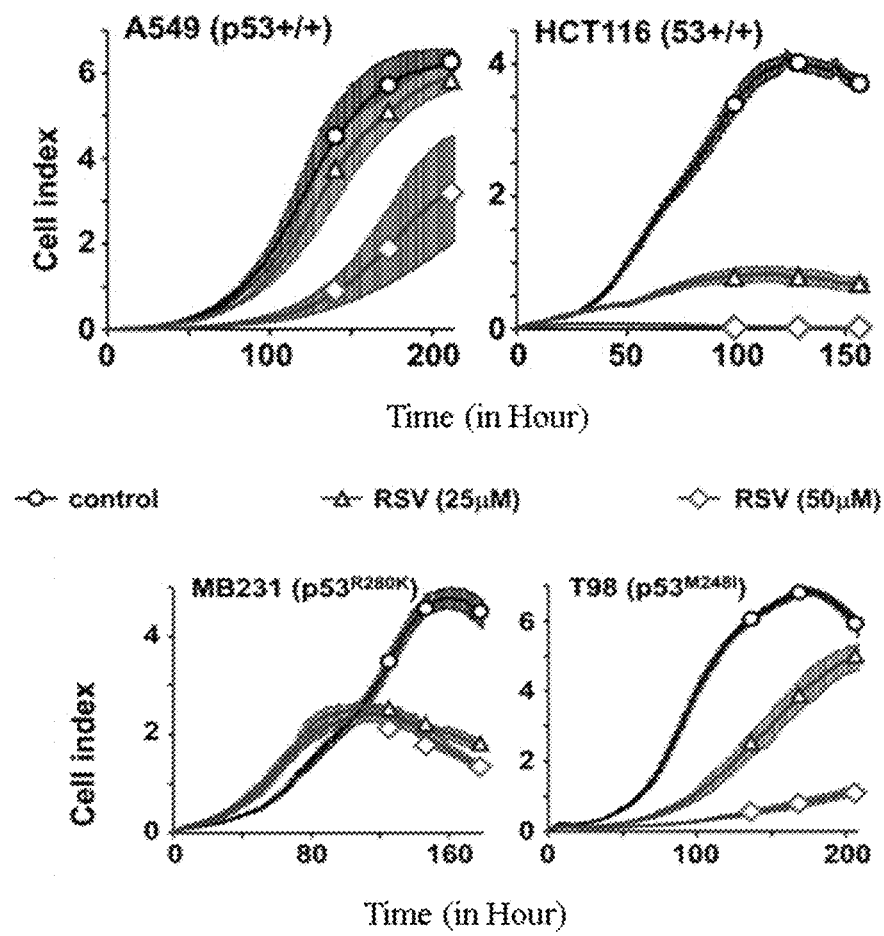
FIG. 9B is an assembly of graphs illustrating 25 and 50 uM of resveratrol was effective in reducing the proliferation of A549 lung cancer cells, HCT116 colon cancer cells, MB231 breast cancer cells and T98 glioblatoma cells.

In Vitro Evaluation of the Effect of Resveratrol on Puf-A Expression and Cancer Cells An in vitro evaluation of the effect of Resveratrol on the expression level of Puf-a protein and cell proliferation in various cancer cells was examined. The following cancer cells were treated with 0, 25 or 50 uM of Resveratrol (commercially available from Sigma, USA): A549 lung cancer cells (p53 proficient), HCT116 colon cancer cells (p53 proficient), MB231 breast cancer cells (p53 deficient) and T98 glioblatoma cells (p53 deficient). The expression of Puf-A protein in these cancer cells was analyzed by western blot and the cell proliferation was measured with a cell proliferation assay performed with xCELLigenece RTCA system (ACEA Biosciences Inc, USA). FIG. 9A is an assembly of Western blot images illustrating 25 and 50 uM of resveratrol reduced the expression of Puf-A in A549 lung cancer cells, HCT116 colon cancer cells, MB231 breast cancer cells and T98 glioblatoma cells. FIG. 9B is an assembly of graphs illustrating 25 and 50 uM of resveratrol reduced the proliferation of A549 lung cancer cells, HCT116 colon cancer cells, MB231 breast cancer cells and T98 glioblatoma cells compare to the control group (no resveratrol).

What is claimed is:

1. A method of inhibiting cancer cells in a subject, comprising the step of contacting a therapeutically effective amount of Puf-A inhibitor with the cancer cell;
wherein the Puf-A inhibitor is a small hairpin RNA (shRNA); and
wherein the polynucleotide encoding the shRNA has a nucleotide sequence at least 90% homologous SEQ ID NO:2 or SEQ ID NO: 3.

2. The method of claim 1, wherein the cancer cells are P-53 deficient.

3. The method of claim 2, wherein the P-53 deficient cancer cells are selected from the group consisting of colorectal cancer, lung cancer, breast cancer and glioblastoma.

4. The method of claim 1, wherein the cancer cells express Puf-A.

5. The method of claim 4, wherein the cancer cells express Puf-A are selected from the group consisting of colorectal, breast, ovarian, cervical, endometrial, carcinoid, head and neck, thyroid, glioma, lymphoma, lung, melanoma, skin, urothelial, renal, stomach, pancreatic and liver cancer.

6. The method of claim 1, wherein the polynucleotide encoding the shRNA is incorporated into a vector.

7. The method of claim 6, wherein the vector is a viral vector.

8. The method of claim 6, wherein the vector is a non-viral vector.

9. The method of claim 1, wherein the Puf-A inhibitor is administered prior to, simultaneously with or after an anti-cancer agent.

10. A polynucleotide, comprising a nucleotide sequence at least 90% homologous to SEQ ID NO:2 or SEQ ID NO:3.

11. A vector, comprising
  a) a promoter; and
  b) a polynucleotide having a nucleotide sequence at least 90% homologous to SEQ ID NO:2 or SEQ ID NO:3.

12. The vector of claim 11, wherein the polynucleotide encodes an shRNA.

13. A pharmaceutical composition, comprising
  (a) the vector, comprising a promoter; and a polynucleotide, wherein the polynucleotide having a nucleotide sequence at least 90% homologous to SEQ ID NO:2 or SEQ ID NO:3; and
  (b) a pharmaceutically acceptable carrier.

14. The pharmaceutical composition of claim 13, wherein the polynucleotide encodes an shRNA.

* * * * *